United States Patent [19]
Suh et al.

[11] Patent Number: 6,150,390
[45] Date of Patent: Nov. 21, 2000

[54] 3-AMINO-1,2-BENZOISOXAZOLE DERIVATIVES, PROCESS FOR PREPARATION, AND USE THEREOF

[75] Inventors: Hong-Suk Suh, Pusan-si; Jae-Ha Ryu; Yong-Nam Han, both of Sungnam-si; Sung-June Yoon, Seoul; Jong-Woo Kim, Kyoungki-di, all of Rep. of Korea

[73] Assignee: Dong Wha Pharm. Ind. Co., Ltd., Seoul, Rep. of Korea

[21] Appl. No.: 09/355,195

[22] PCT Filed: Feb. 4, 1998

[86] PCT No.: PCT/KR98/00023

§ 371 Date: Jul. 21, 1999

§ 102(e) Date: Jul. 21, 1999

[87] PCT Pub. No.: WO98/33779

PCT Pub. Date: Aug. 6, 1998

[30] Foreign Application Priority Data

Feb. 4, 1997 [KR] Rep. of Korea .................. 97/3356

[51] Int. Cl.⁷ .................. A61K 31/423; C07D 261/20
[52] U.S. Cl. .................................. 514/379; 548/241
[58] Field of Search .............. 548/241; 514/379

[56] References Cited

PUBLICATIONS

Journal of Medicinal Chemistry of Jul. 5, 1996, vol. 39, No. 14 Modulators of Leukotriene Biosysthesis and Receptor Activation by Clint D. Brooks and James B. Summers, pp. 2629–2654.

The In Vitro and In Vivo Pharmacologic Activity of the Potent and Selective Leukotriene B4 Receptor Antagonist CP–105696, Dec. 12, 1994, vol. 273, No. 1 by H. J. Showell et al., The Journal of Pharmacology and Experimental Therapeutics, pp. 176–184.

Suh et al., Bioorg. Med. Chem. Lett. (Feb. 18, 1997), 7(4), 389–392, Feb. 1997.

*Primary Examiner*—Laura L. Stockton
*Attorney, Agent, or Firm*—Bachman & LaPointe, P.C.

[57] ABSTRACT

The present invention relates to a novel 3-amino-1,2-benzoisoxazole derivatives, represented by Formula I, LTB-4[leukotriene-B-4; 5(S),12(R)-dihydroxy-6,14-cis-8,10-trans-eicosatetraenoic acid] receptor antagonist, process for preparation thereof, and use thereof for LTB-4 receptor antagonist or therapeutics for osteoporosis.

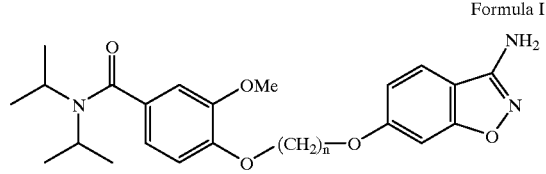

Formula I (in which n is integer of 3–5).

6 Claims, No Drawings

3-AMINO-1,2-BENZOISOXAZOLE DERIVATIVES, PROCESS FOR PREPARATION, AND USE THEREOF

This application is a 371 of PCT/KR98/00023 filed Feb. 4, 1998.

FIELD OF THE INVENTION

The present invention relates to a novel 3-amino-1,2-benzoisoxazole derivatives, represented by Formula I, LTB-4[leukotriene-B-4; 5(S),12(R)-dihydroxy-6,14-cis-8,10-trans-eicosatetraenoic acid] receptor antagonist, process for preparation thereof, and use thereof for LTB-4 receptor antagonist or therapeutics for osteoporosis.

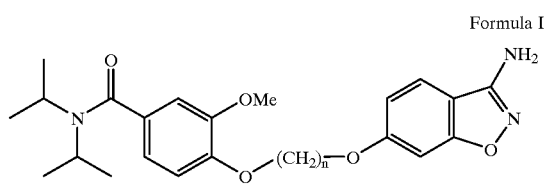

Formula I (in which n is integer of 3–5.)

LTB-4, natural product, is metabolite of arachidonate, produced in the path way of 5-lipoxygenase [Ford-Hutchison, A. W. et al., Nature(London), 286, 264–265, 1980]. LTB-4 induces cohesion and degranulation of neutrophil, and promotes chemical taxis and locomotion of leukocyte, and LTB-4 contracts smooth muscle, and participate in the production of peroxide, and is also detected in a large amount at inflammatory lesions of patient, such as psoriasis, enteritis, rheumatoid arthritis, bronchial asthma, and adult respiratory distress syndrome.

Compound for LTB-4 receptor antagonist, therefore, can be utilized effectively as inhibitor and treating medicine at the above mentioned disease (Clint, D. W. et al., J. Med. Chem. 39, 2629–2654, 1996; Suh, H., U.S. Pat. No. 5,455, 274, 1995).

Usual LTB-4 receptor antagonists were SM-9064 (Namiki, M. et al., Biochem. Siophys. Res. Comm. 138, 540–546, 1986); U-75302 (Morris, J. et al., Tetrahedron Lett. 29, 143–146, 1988); LY-255283 (Herron, D. K. et al., FASEB J. 2, A1110, 1988); SC-41930 (Djuric, S. W. et al., J. Med. Chem. 32, 1145–1147, 1989); LY-223982 (Gapinski, D. M. et al., J. Med. Chem. 33, 2807–2813, 1990); ONO-LB457 (Konno, M. et al., Adv. Prostaglandin, Thromboxane Leukotriene Res. 21, 411–414, 1991); CP-105696 (Showell, H. J. et al., J. Pharmacol. Exper. Ther. 273, 176–184, 1995); CGS-25019C (Morrissey, M. M., Suh, H. U.S. Pat. No. 5,451,700; Brooks, C. D. et al., J. Med. Chem. 39, 2629–2654, 1996); and so on.

It has been reported that CGS-25019C, which is in the highest critical step, have toxicity to stimulate stomach and intestine among the usual antagonist. So, it is necessary to develop a novel LTB-4 receptor antagonist.

Bone maintain necessary bone mass and the structure as a physical support of body, and play a important role as keeping the concentration of $Ca^{2+}$, etc. in blood as a stock of $Ca^{2+}$ and so on.

Bone resorption and remodeling is continuously recycled, to carry out the above functions, and is in the dynamic state of metabolite with resorbing and remodeling of bone. When the remodeling of bone does not equilibrate the resorption of bone, the resorption is relatively superior to the remodeling of bone, and it causes the reduction of bone density and mass to osteoporosis, which is in the state of not maintaining of bony strength. Osteoporosis is very frequently occurred in middle aged and old women.

Therapeutics for osteoporosis, so far, have been developed to inhibit the resorption of bone by inhibiting the action of osteoclast cells. Fracturability by the reduction of bone mass may be not recovered only by inhibiting the resorption of bone. For the ideal treatment of osteoporosis, the recovery from the fracturability, there is necessity that the medicine inhibit the resorption of bone and accelerate the remodeling of bone.

We, inventors have synthesized various compounds and examined their effect of antagonizing LTB-4 receptor and of accelerating the bone formation in order to inhibit and treat the disease relevant to LTB-4 and osteoporosis. As a result, the present inventors completed the invention through synthesizing 3-amino-1,2-benzoisoxazole derivatives, represented by Formula I, and identifying their effect of antagonizing LTB-4 receptor and of accelerating the bone formation.

SUMMARY OF THE INVENTION

The present invention has an object to provide novel 3-amino-1,2-benzoisoxazole derivatives, represented by Formula I.

The present invention has another object to provide process for preparation of 3-amino-1,2-benzoisoxazole derivatives, represented by Formula I.

The present invention has another object to provide pharmaceutical composition containing one of 3-amino-1, 2-benzoisoxazole derivatives, represented by Formula I, in effective amount which can antagonize LTB-4 receptor.

Also, the present invention has another object to pharmaceutical composition containing one of 3-amino-1,2-benzoisoxazole derivatives, represented by Formula I, in effective amount which can accelerate the bone formation.

It should be apparent that another purpose of the present invention and their application be made by those skilled in the art from detailed description of the invention.

DETAILED DESCRIPTION OF THE INVENTION

The present invention will now be described in detail.

Compounds, represented by Formula I, according to the present invention are N,N-diisopropyl-4-[4-(3-aminobenzo[d]isoxazol-6-yloxy)butoxy]-3-methoxybenzamide (HS-1141), represented by Formula II;

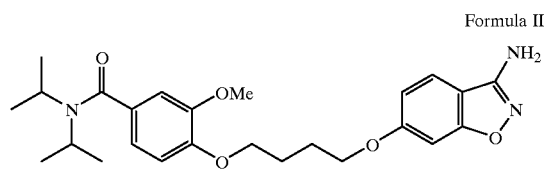

Formula II

N,N-diisopropyl-4-[3-(3-aminobenzo[d]isoxazol-6-yloxy)propoxy]-3-methoxybenzamide (HS-1151), represented by Formula III; and

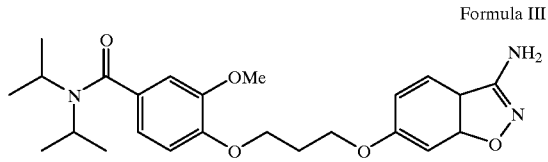

Formula III

N,N-diisopropyl-4-[5-(3-aminobenzo[d]isoxazol-6-yloxy)pentoxy]-3-methoxybenzamide (HS-1132), represented by Formula IV.

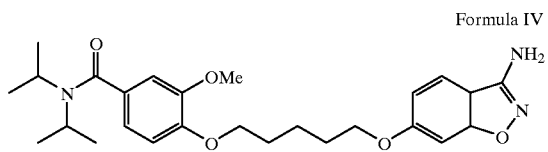

Formula IV

As demonstrated by the following Experiment, compounds of Formula II to IV according to the present invention can be utilized as inhibitor and therapeutics for the disease relevant to LTB-4 or osteoporosis, because the compounds have effects of LTB-4 receptor antagonist and of accelerating the bone formation.

Compounds according to the present invention can be administered in effective amount to inhibit the action of LTB-4 receptor or to treat osteoporosis by various administrable path; and the form and dose thereof can be determined by those skilled in the art in consideration of administrative object; administrable path; and a status and weight of patient.

LTB-4 receptor antagonist or therapeutics for osteoporosis, preferably, contains both one of 3-amino-1,2-benzoisoxazole derivatives, represented by Formula I, and pharmaceutically acceptable carriers. These carriers can be selected from the group comprising the standard pharmaceutically acceptable carriers, which is commonly used in, pasteurized solution, tablet, coated tablet, and capsule. These carriers, typically, contain bulking agent, such as starch, milk, sugar, specific clay, gelatin, stearic acid, talc, vegetable fat or oil, gum and glycols, etc. or other kind of known bulking agent. Also, sweetening agent, coloring additives and other component can be contained in the carriers.

Composition, which contain these carriers, can be formatted by the known method. But, composition, which contain 3-amino-1,2-benzoisoxazole derivatives for LTB-4 receptor antagonist and therapeutics for osteoporosis, has never been reported.

In the present invention, LTB-4 receptor antagonist and therapeutics for osteoporosis containing one of 3-amino-1,2-benzoisoxazole derivatives, can be administered by the known manner, such as oral dose, intravenous, intramuscular, and percutaneous injection, and so on. But it is not limited to these manner.

In carrying out the present invention, 3-amino-1,2-benzoisoxazole derivatives may be contained in a very extensive range of amount in the pharmaceutical composition. Effective amount of 3-amino-1,2-benzo-isoxazole for LTB-4 receptor antagonist or therapeutics for osteoporosis is 10–1000 mg/day. Dose of composition and its frequency can be easily determined by those skilled in the art according to characteristics of administrative form; status and weight of patient; size of inflammatory lesions; path and frequency of administration; and characteristics of specific derivatives to be used.

Process for preparation of compound according to the present invention comprises steps, represented by Scheme I, with the following 4-hydroxy-3-methoxybenzoic acid (1) as starting material, and the specific condition of reaction is shown in the Examples, as follows.

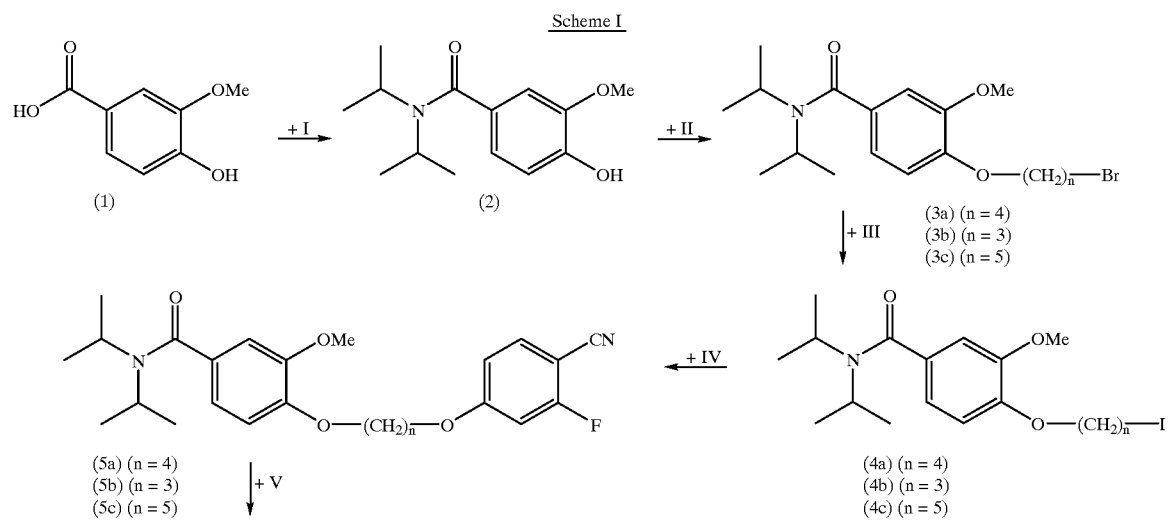

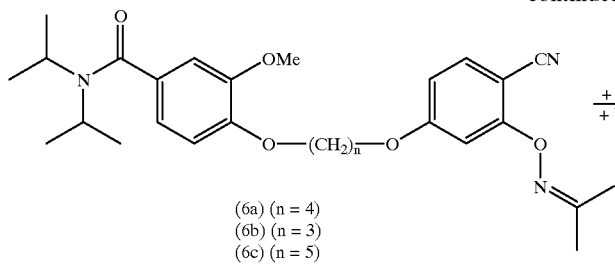
(6a) (n = 4)
(6b) (n = 3)
(6c) (n = 5)

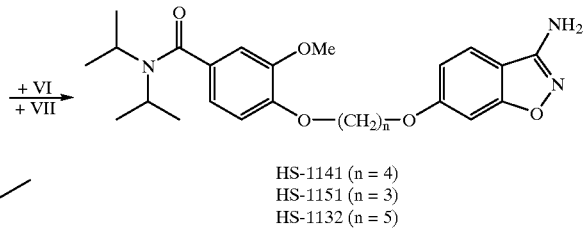
HS-1141 (n = 4)
HS-1151 (n = 3)
HS-1132 (n = 5)

in which I is diisopropylamine;
II is dibromobutane(a), dibromopropane(b) or dibromopentane(c);
III is sodium iodide (NaI);
IV is 2-fluoro-4-hydroxybenzonitrile;
V is acetoneoxime;
VI is hydrochloric acid; and
VII is potassium carbonate ($K_2CO_3$).

The present invention has been described by reference to specific examples chosen for the purpose of illustration, but it is apparent that the present invention should not be limited by the specific disclosure herein.

The abbreviation used in this specification means, as follows:
DMF: dimethyl formamide
DMSO: dimethyl sulfoxide
GF/C: glass fiber filter type C
HBSS media: Hank's balanced salt solution
TMS: tetramethylsilane (reference material of NMR spectrum)

Compounds according to the present invention was identified by mass spectrum and NMR spectrum using NMR spectrometer (made by Varian Co.) according to the method of Lambert (Lambert et al., *Organic Structural Analysis*, Macmillan Pub. Co., NY, 1993).

EXAMPLE 1

Preparation of N,N-diisopropyl-4-[2-isopropylidene Nitro Oxy-benzonitrile-4-yloxy)butoxy]-3-methoxybenzamide [Compound (6a)]

(Step 1) Preparation of N,N-diisopropyl-4-hydroxy-3-methoxybenzamide [Compound (2)]

4-Hydroxy-3-methoxybenzoic acid, compound (1), (5 g, 29.6 mmol) was dissolved in methylene chloride (200 ml), then hereto were added thionyl chloride (20 ml, 272 mmol) and DMF (1 ml, 12.8 mmol), refluxed for 1 hour, and concentrated under reduced pressure. The resultant was dissolved in methylene chloride (200 ml), and hereto was added diisopropylamine (20 ml, 142.8 mmol). It was stirred for 2 hours, diluted in ethyl acetate (500 ml), and washed with aqueous solution of hydrochloric acid (100 ml, 1N) for 2 times and saturated aqueous solution of sodium chloride (130 ml). The resultant organic layer was dried over anhydrous magnesium sulfate, and the solvent was removed. Resultant was purified by column chromatography (ethyl acetate:n-hexane=2:3) to obtain 5.23 g of compound (2) [$R_f$: 0.32, yield: 70%].

$^1$H NMR (CDCl$_3$, 200 MHz) δ 1.20(d, 12H, J=2.6Hz), 3.69(m, 2H), 3.79(s, 3H), 6.74(m, 3H).

$^{13}$C NMR (CDCl$_3$, 200 MHz) δ 20.5, 47.8, 55.6, 110.1, 115.0, 118.4, 129.9, 147.0, 147.3, 169.8.

(Step 2) Preparation of N,N-diisopropyl-4-hydroxy-3-methoxybenzamide [Compound (3a)]

N,N-Diisopropyl-4-hydroxy-3-methoxybenzamide, obtained in the above Step 1, (2.0 g, 7.96 mmol) was dissolved in DMF (30 ml), and hereto was added potassium carbonate (1.32 g, 9.55 mmol). The reaction mixture was stirred for 30 minutes, then hereto was added dibromobutane (1.14 ml, 9.55 mmol), and refluxed for 5 hours. After diluting the reaction mixture with ethyl acetate (20 ml), it was washed with aqueous solution of hydrochloric acid (1N), aqueous solution of sodium chloride, and distilled water. The organic layer was dried over anhydrous magnesium sulfate, and was removed the solvent. The resultant was purified by column chromatography (ethyl acetate:n-hexane=1:1) to obtain 1.9 g of compound (3a) [$R_f$: 0.26, yield: 62%].

(Step 3) Preparation of N,N-diisopropyl-4-(4-iodobutoxy)-3-methoxybenzamide [Compound (4a)]

N,N-Diisopropyl-4-(4-bromobutoxy)-3-methoxybenzamide, obtained by the above Step 2, (1.9 g, 4.92 mmol) was dissolved in acetone (30 ml), and hereto was added sodium iodide (NaI; 1.87 g, 9.84 mmol). The reaction mixture was refluxed for 10 hours, and the solvent was removed. The resultant was dissolved in diethyl ether, and the organic layer was washed with aqueous solution of sodium chloride and distilled water. The organic layer was dried over anhydrous magnesium sulfate, and removed the solvent. The resultant was purified by column chromatography (ethyl acetate:n-hexane=1:1) to obtain 1.41 g of compound (4a) [$R_f$: 0.24, yield: 66%].

(Step 4) Preparation of N,N-diisopropyl-4-[(2-fluorobenzonitrile-4-yloxy)butoxy]-3-methoxybenzamide [Compound (5a)]

2-Fluoro-4-hydroxybenzonitrile (0.403 g, 2.98 mmol) was dissolved in DMF (20 ml), then hereto was added sodium hydride (0.16 g, 3.58 mmol) at 0° C., and stirred for 20 minutes. Compound (4a)(1.41 g, 3.28 mmol) was dissolved in DMF (10 ml), and it was added to the above mixture. The reaction mixture was stirred for 2 hours at room temperature, diluted in ethyl acetate (20 ml), and washed with distilled water for 4 times. The organic layer was dried over anhydrous magnesium sulfate, and the solvent was removed. The resultant was purified by column chromatography (ethyl acetate:n-hexane=1:1) to obtain 0.69 g of compound (5a) [$R_f$: 0.32, yield: 56%].

$^1$H NMR (CDCl$_3$, 200 MHz) δ 1.25–1.45 (m, 12H), 2.00 (m, 2H), 3.72(br, 2H), 3.83(s, 3H), 4.09(m, 4H), 6.72 (m, 2H), 6.85(d, 2H), 7.48(t, 1H, J=7.8Hz).

$^{13}$C NMR (CDCl$_3$, 200 MHz) δ 20.6, 25.4, 25.7, 48.1, 55.8, 68.4, 92.4, 102.5, 109.9, 111.7, 112.2, 114.3, 118.1, 131.6, 134.0, 148.5, 149.1, 161.8, 164.2, 166.9, 170.6.

(Step 5) Preparation of N,N-diisopropyl-4-[2-isopropylidene Nitro Oxy-benzonitrile-4-yloxy)butoxy]-3-methoxybenzamide [Compound (6a)]

Acetoneoxime (0.52 g, 7.15 mmol) was dissolved in DMF (20 ml), and hereto was added potassium t-butoxide (0.80 g, 7.15 mmol). The reaction mixture was stirred for 30 minutes, then hereto was added compound (5a)(0.586 g, 1.43 mmol), and stirred for 5 hours. The resultant was poured into the mixed solution of aqueous solution of ammonium chloride and diethyl ether, then the organic layer was separated and washed with distilled water for 3 times. The organic layer was dried over anhydrous magnesium sulfate, and the solvent was removed. The resultant was purified by column chromatography (ethyl acetate:n-hexane=1:1) to obtain 0.636 g of compound (6a) [$R_f$: 0.32, yield: 96%].

$^1$H NMR (CDCl$_3$, 200 MHz) δ 1.20–1.45(m, 12H), 2.00–2.10(m, 4H), 2.05(s, 3H), 3.74(br, 2H), 3.86(s, 3H), 4.11(t, 4H, J=5.78Hz), 6.54(dd, 1H, J=2.32Hz, 8.60Hz), 6.86(m, 3H), 7.08(d, 1H, J=2.32Hz), 7.43(d, 1H, J=8.60Hz).

$^{13}$C NMR (CDCl$_3$, 200 MHz) δ 15.9, 20.2, 21.0, 25.1, 25.3, 47.8, 55.4, 67.5, 67.9, 90.2, 100.1, 108.1, 109.5, 112.0, 115.9, 117.8, 131.1, 133.2, 148.3, 148.8, 160.7, 162.0, 163.4, 170.1.

EXAMPLE 2

Preparation of N,N-diisopropyl-4-[4-(3-aminobenzo [d]isoxazol-6-yloxy)butoxy]-3-methoxybenzamide (HS-1141)

Compound (6a), obtained by the Example 1, (0.636 g, 1.37 mmol) was added to the mixed solution of ethanol (10 ml) and aqueous solution of hydrochloric acid (5%, 10 ml), then heated to 50° C. and left for 10 hours. The reaction mixture was concentrated under reduced pressure to remove ethanol, and the resultant aqueous solution was turned into basic with aqueous solution of potassium carbonate. It was extracted with ethyl acetate for 3 times, and the organic layer was washed with distilled water. The organic layer was dried over anhydrous magnesium sulfate, and the solvent was removed. The resultant was purified by column chromatography (ethyl acetate:n-hexane=1:1) to obtain 0.401 g of desired compound, HS-1141 [$R_f$: 0.32, yield: 64%].

$^1$H NMR (CDCl$_3$, 200 MHz) δ 1.20–1.50(m, 12H), 2.05 (m, 4H), 3.75(br, 2H), 3.85(s, 3H), 4.13(m, 4H), 6.86–6.79 (m, 5H), 7.35(d, 1H, J=8.4Hz).

$^{13}$C NMR (CDCl$_3$, 200 MHz) δ 20.7, 25.8, 48.0, 55.8, 67.9, 68.4, 93.3, 109.2, 109.8, 112.1, 118.1, 120.6, 131.4, 148.6, 149.1, 157.8, 161.4, 164.7, 170.8.

Here is the result of analysis of HS-1141 by mass spectrum.

Calculated: C(65.62), H(7.71), N(9.18).
Found: C(65.70), H(7.49), N(8.87).

EXAMPLE 3

Preparation of N,N-diisopropyl-4-[3-(3-aminobenzo [d]isoxazol-6-yloxy)propoxy]-3-methoxybenzamide (HS-1151)

Compound (3b) was prepared by the same condition of Step 2 in the Example 1, except for replacing dibromobutane with dibromo-propane, and from this compound (6b) was prepared by the same condition of Example 1 through the intermediates, compound (3b), (4b), and (5b).

HS-1151 was obtained by the same condition of Example 2, except for replacing compound (6a) with compound (6b) [$R_f$: 0.26 (ethyl acetate:n-hexane=1:1)].

$^1$H NMR (CDCl$_3$, 200 MHz) δ 1.25–1.91(m, 12H), 2.35(t, 2H), 3.72(br, 2H), 3.86(s, 3H), 4.24(t, 4H, J=5.8Hz), 6.82–6.91(m, 5H), 7.35(d, 1H, J=8.2Hz)

$^{13}$C NMR (CDCl$_3$, 200 MHz) δ 20.7, 28.9, 48.3, 55.8, 64.8, 65.4, 93.6, 109.4, 109.9, 112.6, 112.9, 118.1, 120.6, 131.7, 148.6, 149.2, 157.8, 161.4, 164.6, 170.8

EXAMPLE 4

Preparation of N,N-diisopropyl-4-[5-(3-aminobenzo [d]isoxazol-6-yloxy)pentoxy]-3-methoxybenzamide (HS-1132)

Compound (3c) was prepared by the same condition of Step 2 in the Example 1, except for replacing dibromobutane with dibromopentane, and from this compound (6c) was prepared by the same condition of Example 1 through the intermediate, compound (3c), (4c) and (5c).

HS-1132 was obtained by the same condition of Example 2, except for replacing compound (6a) with compound (6c) [$R_f$: 0.32 (ethyl acetate:n-hexane=1:1)].

$^1$H NMR (CDCl$_3$, 200 MHz) δ 1.34(m, 12H), 1.68(t, 2H), 1.90(m, 4H), 3.72 (br, 2H), 3.84(s, 3H), 4.02(t, 4H J=6.2Hz), 6.86–6.74(m, 5H), 7.34(d, 1H, J=8.4Hz).

$^{13}$C NMR (CDCl$_3$, 200 MHz) δ 20.6, 22.4, 28.5, 28.6, 49.1, 55.7, 68.0, 68.5, 93.2, 109.3, 109.8, 112.2, 112.7, 118.1, 120.7, 131.7, 148.7, 149.0, 157.9, 161.4, 164.5, 170.7.

EXPERIMENT 1

Test on Antagonizing Action for LTB-4 Receptor

Antagonizing action of compounds, which are obtained by the above Example 2 to 4, for LTB-4 receptor was measured, as follows:

Neutrophil was separated from whole blood of human by precipitation using "Dextran T-500", and by the inclined centrifugation with Ficoll/Paque (Pharmacia Co.) Boyum, *Scan. J. Clin. Lab. Invest.*, 21 suppl. 97, 77–89, 1989).

Mixed erythrocyte was removed by hemolysis of hypotonic solution. Final neutrophil was dispersed to 3×10$^7$ cell/ml in HBSS media and used for measuring the antagonizing action for LTB-4 receptor.

Measurement of antagonizing action for LTB-4 was followed by the reported method (Tsai et al., *Prostaglandins*, 38, 655–674, 1989), and concrete experimental method was mentioned, as follows:

0.5 nM of [$^3$H]-LTB-4 (200 Ci/mmol), test sample to measure the antagonizing action for LTB-4 receptor, and cell dispersed in HBSS media was added to 12 mm×75 mm of polyethylene tube (final volume: 200 μl), and left in ice bath for 45 minutes.

To separate [$^3$H]-LTB-4 bound to neutrophil and isolated [$^3$H]-LTB-4 not bound to neutrophil, the above mixture was filtered through GF/C filter (made by Wattman Co.). Filter paper was washed with pH 7.4 of cold Tris-buffer solution (5 ml) for 3 times, dried, and measured radioactivity. The selective binding of LTB-4 to neutrophil can be detected by the difference between radioactivities without antagonist in case that LTB-4 was totally bound to neutrophil, and that LTB-4 was bound to neutrophil in addition of radioisotope-unlabeled LTB-4 1000 times.

Degree of antagonizing action in Table I is represented as inhibitory degree of selective binding which is % value of samples to the control, and IC$_{50}$ was meant to concentration of 50% of antagonizing in binding to receptor.

To compare the antagonizing action of compounds according to the present invention with that of existing antagonist, CGS-25019C, known compound was used (Morrissey, M. M., and Suh, H., U.S. Pat. No. 5,451,700; Brooks, C. D. et al., J. Med. Chem. 39, 2629–2654, 1996)

TABLE I

| HS compounds | Degree of inhibition (%) | | | $IC_{50}$ |
|---|---|---|---|---|
| | 10 nM | 100 nM | 1 μM | |
| HS-1151 | <10 | 37 | 92 | |
| HS-1141 | 64 | 95 | 99 | 7 nM |
| HS-1132 | <10 | 10 | 90 | |
| CGS-25019C | 11 | 68 | 97 | 80 nM |

From the above Table I, it would be understood that the effect of antagonizing action of the compound of the present invention for LTB-4 receptor was similar to or better (in case of HS-1141) than the known compound, CGS-25019C.

EXPERIMENT 2

Evaluation of Bonelike Nodule Forming

Approximately 30 of calvariae of fetal rat, removed all the tissue, was dissolved in 5 ml sterilized colagenase (0.1%) and trypsin solution (0.05%) at 37° C. 20 Minutes after dissolving, the released cells were collected, and hereto was added fetal serum to the same amount. This procedure was carried out for 3–6 times in every 20 minutes to collect the isolated cells. Collected cells were separated by centrifugation (400 Kg) for 5 minutes and it was suspended in α-MEM media, containing 10% (v/v) fetal bovine serum. Collected cells were cultivated in petri dish for 2–3 days, then separated with trypsin, and it were placed in 96 wells to $2.0 \times 10^3$ cells/100 μl in each well.

After cultivating the cells for 2–3 days, the media were changed to 5% fetal calf serum, 150 μg/ml ascorbic acid and 5 mM β-glycerophosphate, plus or minus sample (HS-1141). The control was in wells without the sample, and this time was arbitrarily set as day. Activity can be measured by the comparison of number of nodule and area of it relatively, and it was shown in Table II. Formed nodule was analyzed with image analyzer (Biorad Co., U.S.A.); camcorder (SONY Co.); and microscope (Leitz Co.).

TABLE II

| Sample | Concentration (M) | Number of nodule (No.) | Area of nodule ($mm^2$) |
|---|---|---|---|
| The control | — | 10.04 ± 1.23 | 0.12 ± 0.026 |
| HS-1141 | 10-8 | 22.80 ± 4.71 | 0.273 ± 0.019 |
| | 10-9 | 24.00 ± 4.04 | 0.379 ± 0.068 |
| | 10-10 | 19.40 ± 1.29 | 0.320 ± 0.082 |
| | 10-11 | 25.67 ± 3.54 | 0.342 ± 0.065 |

From the above Table II, it is apparent that remodeling of bonelike nodule was increased in over than 2 times by HS-1141. Therefore, it is understood that HS-1141 stimulate the bone formation effectively.

Meanwhile, test on toxicity to the compounds of this invention was carried out.

Sample, the compounds of this invention, was dissolved in distilled water, and this solution was injected to rats (5/group). Then the death rate was measured by observing for 14 days after injection.

Lethal dose of 50% ($LD_{50}$) of the compounds of this invention was 1 g/kg.

The compounds of this invention especially accelerate the remodeling of bone in concentration, which is 10,000 times less than concentration of cell toxicity.

Therefore, the compounds of this invention can be therapeutics for osteoporosis as a stimulant of bone formation.

Effects of the Invention

As apparent from the above Experiment, it was found that the compound, represented by Formula I, antagonize LTB-4 receptor and stimulate the bone formation effectively. Therefore, it is expected that good inhibitory and treating effect for the numerous disease relevant to LTB-4 or osteoporosis can be obtained through containing the compound of this invention.

The compounds of this invention can especially stimulate the formation of bonelike nodule, so it can be usefully utilized as therapeutics for osteoporosis.

What is claimed is:

1. 3-Amino-1,2-benzoisoxazole derivatives, represented by Formula I, as follows:

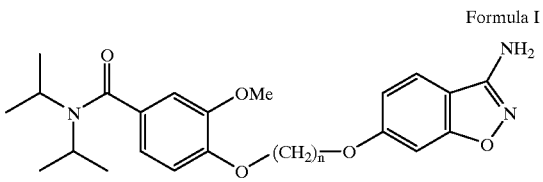

Formula I in which n is an integer of 3–5.

2. LTB-4 receptor antagonist composition containing a 3-amino-1,2-benzoisoxazole derivative, represented by Formula I, in effective amount and a pharmaceutical carrier

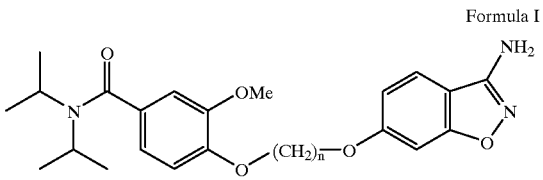

Formula I in which n is an integer of 3–5.

3. LTB-4 receptor antagonist composition as claimed in claim 2, wherein one of 3-amino-1,2-benzoisoxazole derivatives is N,N-diisopropyl-4-[4-(3-amino-benzo[d]isoxazol-6-yloxy)butoxy]-3-methoxy-benzamide (HS-1141).

4. A method of treating osteoporosis by administering to a patient in need thereof an effective amount of a 3-amino-1,2-benzoisoxazole derivative, represented by Formula I

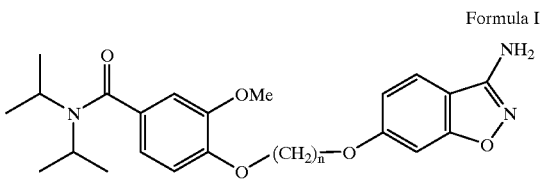

Formula I in which n is an integer of 3–5.

5. A method of treating osteoporosis as claimed in claim 4, wherein one of 3-amino-1,2-benzoisoxazole derivatives is N,N-diisopropyl-4-[4-(3-amino-benzo[d]isoxazol-6-yloxy) butoxy]-3-methoxy-benzamide (HS-1141).

6. A process for preparation of a 3-amino-1,2-benzoisoxazole derivative, represented by Scheme I, as follows:

Scheme I
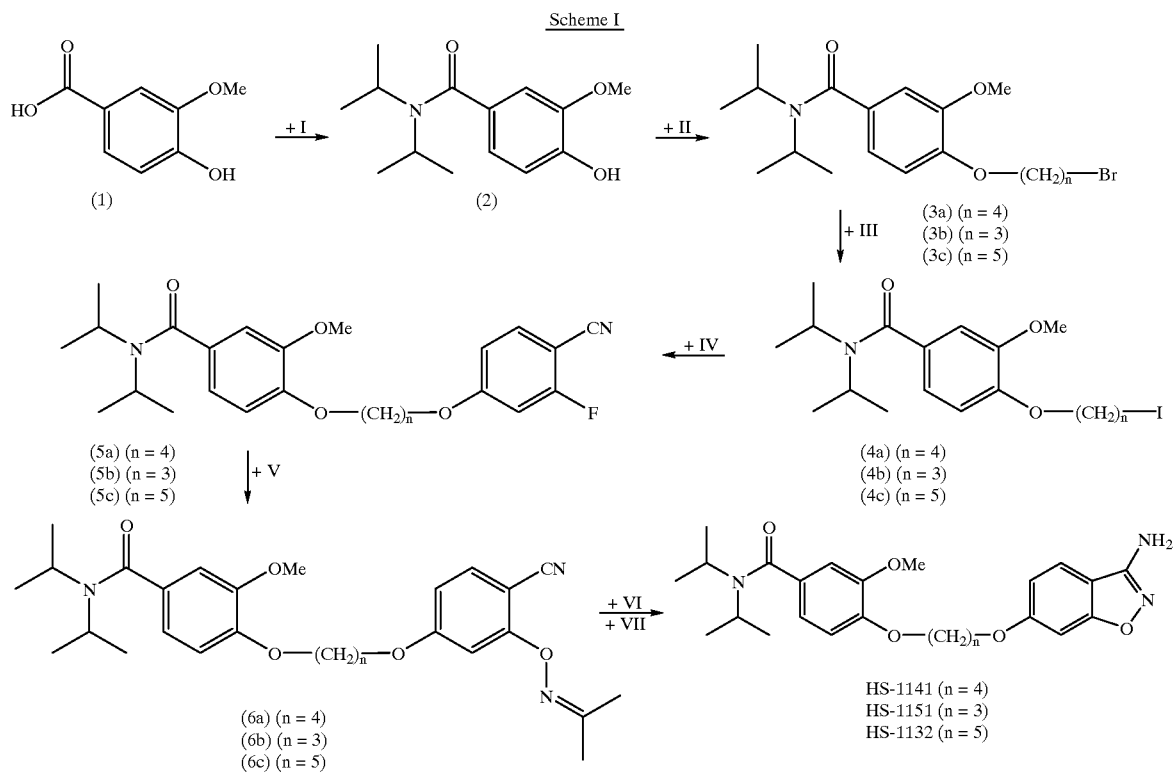
(5a) (n = 4)
(5b) (n = 3)
(5c) (n = 5)
(6a) (n = 4)
(6b) (n = 3)
(6c) (n = 5)
(4a) (n = 4)
(4b) (n = 3)
(4c) (n = 5)
HS-1141 (n = 4)
HS-1151 (n = 3)
HS-1132 (n = 5)
in which, I is diisopropylamine;
II is dibromobutane(a), dibromopropane(b) or dibromopentane(c);
III is sodium iodide (NaI);
IV is 2-fluoro-4-hydroxybenzonitrile;
V is acetoneoxime;
VI is hydrochloric acid; and
VII is potassium carbonate ($K_2CO_3$).
* * * * *